US010215737B2

United States Patent
Coleman et al.

(10) Patent No.: US 10,215,737 B2
(45) Date of Patent: Feb. 26, 2019

(54) APPARATUS FOR AND METHOD OF GAS ANALYSIS

(71) Applicant: Weatherford Switzerland Trading and Development GmbH, Zug (CH)

(72) Inventors: Dennis D. Coleman, Champaign, IL (US); John Boettcher, Champaign, IL (US); Gavin Atlas Steele, IV, White Heath, IL (US)

(73) Assignee: WEATHERFORD SWITZERLAND TRADING AND DEVELOPMENT GMBH, Zug (CH)

( * ) Notice: Subject to any disclaimer, the term of this patent is extended or adjusted under 35 U.S.C. 154(b) by 108 days.

(21) Appl. No.: 15/096,913

(22) Filed: Apr. 12, 2016

(65) Prior Publication Data
US 2016/0223499 A1     Aug. 4, 2016

Related U.S. Application Data

(62) Division of application No. 14/193,941, filed on Feb. 28, 2014, now Pat. No. 9,341,606.
(Continued)

(51) Int. Cl.
*G01N 33/00*     (2006.01)
*G01N 30/06*     (2006.01)
(Continued)

(52) U.S. Cl.
CPC ............. *G01N 30/06* (2013.01); *G01N 30/74* (2013.01); *G01N 30/84* (2013.01); *G01N 30/88* (2013.01);
(Continued)

(58) Field of Classification Search
CPC .......... G01N 33/0047; G01N 33/0011; G01N 33/0036; G01N 33/0027; G01N 33/0009; G01N 33/0004; G01N 33/00
(Continued)

(56) References Cited

U.S. PATENT DOCUMENTS

| 3,225,520 A | 12/1965 | Burow |
| 3,403,978 A | 10/1968 | Favre |

(Continued)

FOREIGN PATENT DOCUMENTS

WO     8909486 A1     10/1989

OTHER PUBLICATIONS

Snyder et al, Cavity Ring-Down Spectroscopy as a Detector for Liquid Chromatography, Anal. Chem. 2003, 75, 3086-3091.*
(Continued)

*Primary Examiner* — Christine T Mui
(74) *Attorney, Agent, or Firm* — Patterson & Sheridan, LLP

(57) ABSTRACT

A method for preparing a sample for analysis includes separating a gas sample into at least one component sample in a separation unit. The output of the at least one component sample from the separation unit is detected, for example, using a thermal conductivity detector. A hydrocarbon in the component sample is combusted in a combustion unit to generate a combustion product. The at least one component sample is collected in a sample collector and supplied to an analysis unit. In some embodiments, the analysis unit may be used to determine an isotopic ratio of the at least one component sample.

17 Claims, 4 Drawing Sheets

Related U.S. Application Data

(60) Provisional application No. 61/771,349, filed on Mar. 1, 2013.

(51) Int. Cl.
*G01N 30/74* (2006.01)
*G01N 30/84* (2006.01)
*G01N 30/88* (2006.01)
*G01N 30/66* (2006.01)
*G01N 30/02* (2006.01)

(52) U.S. Cl.
CPC ..... *G01N 33/0011* (2013.01); *G01N 33/0047* (2013.01); *G01N 30/66* (2013.01); *G01N 2030/025* (2013.01); *G01N 2030/8854* (2013.01); *Y10T 436/214* (2015.01); *Y10T 436/25875* (2015.01)

(58) Field of Classification Search
USPC .......................................... 436/141, 158, 181
See application file for complete search history.

(56) References Cited

U.S. PATENT DOCUMENTS

| | | |
|---|---|---|
| 3,739,553 A | 6/1973 | Aine |
| 3,840,341 A | 10/1974 | Rogers |
| 6,723,056 B1 | 4/2004 | Alving et al. |
| 2007/0273882 A1 | 11/2007 | Smith |
| 2008/0260587 A1* | 10/2008 | Coleman ................ G01N 30/88 422/89 |
| 2008/0276686 A1 | 11/2008 | Kumazawa et al. |
| 2010/0055802 A1* | 3/2010 | Zare ....................... G01N 21/39 436/158 |
| 2012/0304734 A1 | 12/2012 | Takamoto et al. |
| 2013/0064715 A1 | 3/2013 | Calleri |

OTHER PUBLICATIONS

European Search Report dated May 14, 2014, issued in European counterpart Application No. EP 14157037.4, 8 pages.

Leroy Ellis et al., "Mud Gas Isotope Logging (MGIL) Assists in Oil and Gas Drilling Operations", Oil and Gas Journal, Pennwell, Houston, TX, US, vol. 101, No. 21, May 26, 2003, pp. 32-41, XP001199696.

Owen A. Sherwood et al., "Compound-Specific Stable Isotope Analysis of Natural and Produced Hydrocarbon Gases Srrounding Oil and Gas Operations", In: Imma Ferrer et al., "Comprehensive Analytical Chemistry", Oct. 23, 2013, Elsevier, Amsterdam, vol. 61, pp. 347-372, XP009177923.

Austrailian Exam Report for Patent Application No. 2014201079, dated Jul. 15, 2014.

European Office Action dated Oct. 5, 2017, mailed in counterpart European Application No. 14157037.4, 4 pages.

* cited by examiner

APPARATUS FOR AND METHOD OF GAS ANALYSIS

BACKGROUND

Field

The present disclosure generally relates to an apparatus and method for preparing and analyzing gaseous samples.

Description of the Related Art

In oil and gas extraction, drilling a wellbore generally includes circulating a mud or mud-like substance around the drill bit during drilling operations. This mud or mud-like substance is generally referred to as "drilling mud" and has a variety of potential formulations. Drilling mud serves a number of functions in drilling operations, such as, for example, temperature control of the drill bit, removal of drill cuttings, and counterbalancing formation pressures via hydrostatic pressure.

During drilling operations, it is a common practice to analyze the drilling mud that is returned to the surface after being in proximity to the drill bit. This analysis provides a means for gathering information about the formation through which the wellbore is being drilled. Specifically, oil and gas explorers are often interested in analysis of gases evolved or extracted from the drilling mud. Gas obtained from drilling mud is commonly referred to as "mudgas," and analysis of such gas may be referred to as "mudgas analysis." Mudgas analysis can be used, for example, to detect the presence of hydrocarbons in the wellbore.

When mudgas analysis is performed on samples corresponding to various wellbore depths, mudgas compositions may help to indicate "pay zones" (hydrocarbon-rich zones) within the formation or otherwise to characterize the formation. A mudgas analysis of particular interest in oil and gas exploration is the isotopic analysis of hydrocarbons present in mud samples. For example, the $^{13}C/^{12}C$ ratio of methane in the mudgas may indicate whether the hydrocarbons present in the sample originate from biogenic or thermogenic processes, which in turn may indicate whether liquid petroleum is present in the formation. Additionally, biogenic hydrocarbons are more likely to be spurious indications of recoverable hydrocarbon deposits.

Current methods of mudgas analysis typically require expensive, delicate, and large equipment that is unsuitable or incompatible with drill site operations, thus, generally, mudgas analysis is conducted in laboratories located away from the drill site. Offsite mudgas analysis can result in significant delays between the sampling time and return of results. Delays hinder the usefulness of mudgas analysis in drilling operations, as such an apparatus and a method allowing reliable analytical results on variable feedstocks, such as mudgas, to be quickly obtained is required.

SUMMARY

Embodiments provide an apparatus and method allowing reliable analytic results on variable feedstock samples using alternative analytic methods to GC-C-IRMS.

In one embodiment, an apparatus for preparing a gas sample for analysis includes a separation unit having a chromatographic column. The chromatographic column is configured to separate the gas sample into a component sample or component samples. The apparatus also includes a thermal conductivity detector to detect the output of component samples from the separation unit. Also included, is a component sample collection unit having a sample collector to collect at least one component sample and an outlet for distributing the at least one component sample from the sample collector for analysis.

The apparatus for preparing a gas sample for analysis may optionally include a combustion unit to convert a hydrocarbon in the component sample into carbon dioxide and a methanizer to convert carbon dioxide into methane.

In another embodiment, a gas sample analyzer apparatus, includes a separation unit with a chromatographic column configured to separate a gas sample into one or more component sample; a thermal conductivity detector to detect an output of the one or more component sample from the separation unit; a component sample collection unit to collect the one or more component sample in a sample collector; and an analysis unit to analyze the one or more component sample collected in the sample collector.

In still another embodiment, a method of preparing a gas sample for analysis includes steps of separating a gas sample into one or more component sample; collecting the one or more component samples in a sample collector; and supplying one or more component samples in the sample collector to an analysis unit.

DETAILED DESCRIPTION

Figure 1:
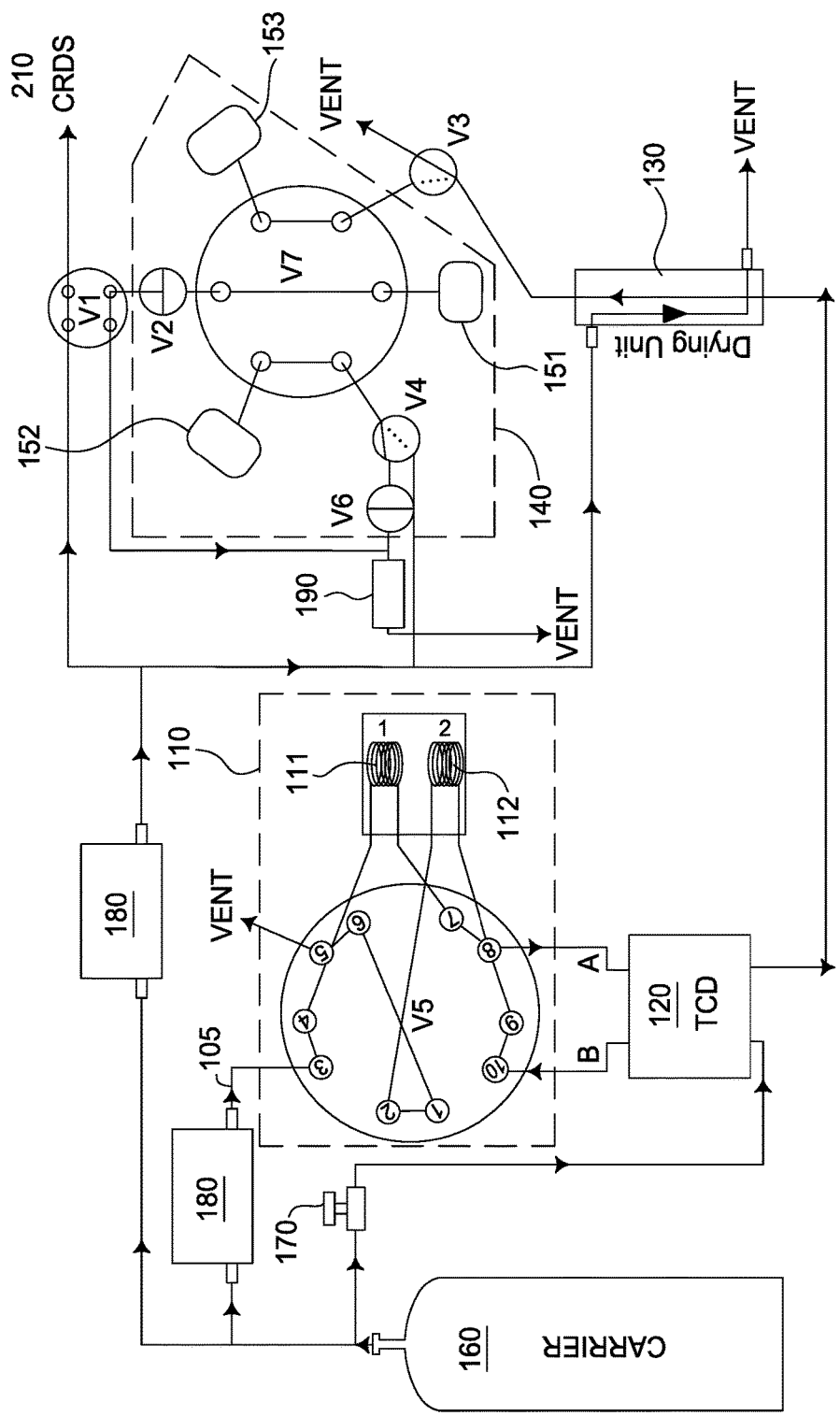
FIG. 1 is a conceptual schematic diagram depicting a first embodiment of an apparatus for preparing a gas sample for analysis.

In the following description, numerous specific details are included in example embodiments to aid understanding of the present disclosure. However, it will be apparent to one skilled in the art that the present inventions may be practiced without one or more of these specific details. In other instances, description of well-known features may have not been included to aid understanding of the present disclosure.

Isotopic analysis of gases extracted from drilling mud is research tool used in oil and gas exploration. But, as currently practiced, mudgas samples are typically collected at the drill site, then shipped offsite to a laboratory for analysis. Shipping samples from the drill site to an offsite laboratory is problematic because mudgas samples are frequently flammable and must be treated as hazardous materials during shipping. The shipment of hazardous materials can be expensive or even, in some instances, prohibited by regulation or ordinance. Even when sample shipment is allowed, drill sites are frequently in remote or inaccessible areas, making it difficult to quickly ship mudgas samples. In some cases, it may require several days or weeks to ship samples to an offsite laboratory making it possible that analytic results from the mudgas samples may not even be available until after well completion, which may cause the well to have a sub-optimal design.

It is preferable to provide mudgas analysis as quickly as possible to allow drillers to make decisions about well design and completion efforts with as much information about the formation as possible. As discussed, quick analysis of mudgas samples will generally require the analysis to be conducted at or near the drill site. Unfortunately, many analytic techniques are not compatible with common drill site environments. For example, performing isotopic analysis on mudgas has traditionally required the use of gas chromatography-combustion-isotope ratio mass spectrometry ("GC-C-IRMS"), which has not been successfully developed for drill site usage after many years of attempts.

Systems capable of performing GC-C-IRMS are generally, large (approximately 1 cubic meter), delicate, and expensive instruments, not suitable for placement at a drill site. There have been several attempts to develop miniature mass spectrometers that might be used in this application, but no attempt has been successful. Consequently, isotopic analysis has typically remained an offsite analytic method and the potential usefulness of the method has been hindered.

Possible replacements for GC-C-IRMS methods are in development and have recently been improving to the point that precision and accuracy is comparable, under controlled laboratory conditions, to results obtained with GC-C-IRMS. Specifically, laser spectrometry techniques have been developed into instruments that are smaller and more robust than the GC-C-IRMS instruments, meaning laser spectrometers are candidates for placement at drill sites. Additionally, laser spectrometers can be used to perform isotopic analysis on several different chemical species, including carbon dioxide ($CO_2$), methane ($CH_4$), and water ($H_2O$), which is a significant advantage over GC-C-IRMS instruments that can only directly analyze carbon dioxide and hydrogen.

Methane is a obviously a component of particular interest in oil and gas exploration, but prior experience with laser spectrometers has generally shown that isotopic analysis of methane using a laser spectrometer on mudgas produces unreliable, even spurious results. Specifically, results from carbon isotope analysis using a cavity ring down spectrometer ("CRDS") on raw, unpurified mudgas flows indicate analytic results vary depending on the type of drilling mud used in drilling operations. Results on raw, unpurified mudgas flows in CRDS systems have been thought generally unreliable.

First Example Embodiment

FIG. 1 depicts, in schematic diagram, a first embodiment of an apparatus for preparing a gas sample for analysis. The apparatus, as depicted, receives a gas sample via injection port 105. The gas sample is supplied to a separation unit 110, such as a gas chromatographic column, which separates the sample into various components. When the separation unit 110 comprises a gas chromatographic column, separation is based on the retention time of each component within the column.

After each component is eluted from the separation unit 110, the component sample travels, via piping or tubing, through a thermal conductivity detector ("TCD") 120 and then a drying unit 130. The TCD 120 detects when components pass through the unit and can signal or trigger the collection of specific components. After passing through the drying unit 130, the component passes into a sample collection unit 140 where the component is collected in a sample collector, such as the depicted expandable gas bag 151, 152, or 153. After collection, the component can be distributed for analysis in, for example, a CRDS system 210 (also referred to as an analysis unit 210).

As depicted in the FIG. 1, the example apparatus includes a separation unit 110 with two gas chromatographic columns ("GC columns") 111 and 112. The apparatus may instead include a single column, or may include more than two columns, if desired. Other separation methods besides chromatography could potentially be used for separating the gas sample into components, but chromatographic methods are relatively easy to implement and have achieved acceptable results.

Figure 4:
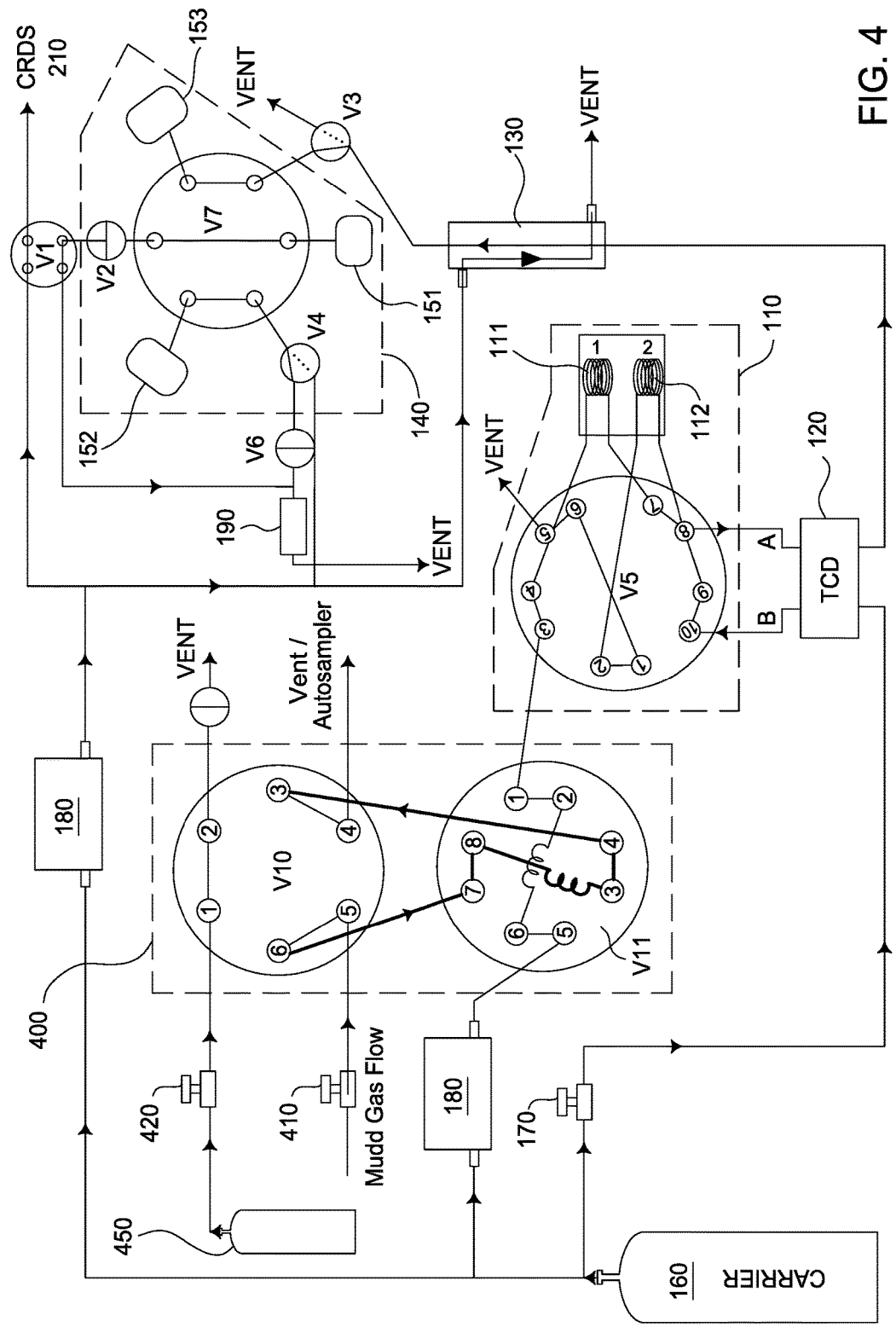
FIG. 4 is a conceptual schematic diagram depicting a fourth embodiment of an apparatus for preparing a gas sample for analysis.

Here, the separation unit 110 is configured to accept a gas sample via an injection port 105, but the invention is not limited to such a configuration (see, e.g. FIG. 4). The gas sample could be input to the separation unit 110 by a variety of means, including piping or tubing connected to a sample source. The gas sample could be input into the separation unit 110 as a single pulse or a series of pulses or as a continuous flow.

In this example, the gas sample can be a mudgas sample extracted or evolved from drilling mud used in oil and gas drilling operations. The sample may contain various components, such as hydrocarbons, carbon dioxide, and water. The hydrocarbon component can include, for example, relatively light components, such, methane and ethane, as well as relatively heavy components such as, propane and butane. In other embodiments, the gas sample could be a wellhead gas, pipeline gas, soil gas, or gas extracted from groundwater, and the present disclosure is not limited any particular source for the gas sample.

The exact composition of the sample will generally be unknown when extracted or evolved from the drilling mud. But in some instances, it may be appropriate to pre-treat the gas sample to remove or reduce certain potential components (e.g., excessive water vapor, particulates, or significantly corrosive or hazardous components) prior to input to the separation unit.

As mentioned, the separation unit 110 depicted in FIG. 1 has two chromatographic columns 111 and 112. As depicted, the separation unit 110 also has a valve system V5 that allows a gas sample to be fed to either of the columns 111 or 112. This is desirable because sample dwell times in the columns may be relatively long and the use of two columns increases the number of samples that can be processed over a given time. The valve system V5 of the separation unit 110 also allows for the GC columns 111 and 112 to be back-flushed with a carrier gas to speed the removal of sample components with long column dwell times that do not need to be collected or analyzed.

The separation unit 110 depicted in FIG. 1 includes a carrier gas input feed stream. A GC-C-IRMS-based apparatus generally requires the carrier gas to be high-purity helium (He), hydrogen ($H_2$), or nitrogen ($N_2$). As an advantage of the present embodiment, the carrier gas need not be one of these expensive gases, but rather may be purified air, easily obtainable using a compressor and common air purification techniques for the removal of hydrocarbons and carbon dioxide. The carrier gas can also be nitrogen having comparatively relaxed purity requirements.

Here, the carrier gas is depicted in FIG. 1 as supplied from a storage reservoir or gas tank 160 via needle valve 170 and the injection port 105. According to the present disclosure, it is not necessary for the carrier gas to be supplied from a storage reservoir or gas tank 160, rather one of the advantages of the present embodiment is the carrier gas can be compressed, purified air, which could be continuously supplied rather than from a gas tank or storage reservoir.

The flow of carrier gas to various apparatus elements can be controlled by various valves (e.g., a needle valve 170, valve V1, valve V2, valve V3, valve V4) and flow controllers 180 as known in the art. The carrier gas can also be supplied to an attached or integrated analysis unit 210, if necessary or desired.

The drying unit 130 depicted in FIG. 1 ("Drying Unit"), is used to remove water vapor from the component samples prior to collection. The specific structure and type of drying unit 130 is not of particular importance. The drying unit 130 serves to stabilize samples by removing water that might condense during sample collection or analysis. As indicated in FIG. 1, the example drying unit 130 includes a Nafion membrane. Nafion is a sulfonated tetrafluoroethylene based fluoropolymer-copolymer suitable for use in this application due to its resistance to chemical degradation. Nafion is cited as an example only and other materials are also suitable and contemplated.

After the component sample is dried, it is input to a sample collection unit 140. The example sample collection unit depicted in FIG. 1 has a valve system (V2, V3, V4, V6, V7) that allows a component to be collected in a first sample collector 153 (also referred to as "Bag 3") while a previously collected component is supplied from a second sample collector 151 (also referred to as "Bag 1") for analysis by an analysis unit 210 (e.g., a CRDS unit 210). The sample collection unit 140 depicted in FIG. 1 also allows a third sample collector 152 (also referred to as "Bag 2") to be cleaned and prepared for the next collection while collection and distribution of other components is being carried out with using the first sample collector 153 and second sample collector 151. The valve system allows the third sample collector 152 to be evacuated by connection to a vacuum source 190, then to be purged with carrier gas. The evacuation-purge cycle can be performed repeatedly, if desired.

In the example, depicted in FIG. 1, the sample collectors are expandable gas bags. These gas bags may preferably be metalized plastic bags, but any container capable of retaining the component gas may be used.

The operation of the apparatus depicted in FIG. 1 can be automated such that separation, purification, and collection of gas sample components can be performed without intervention by a human operator. In such a case, either a special-use computer or a general computer running appropriate software can be used to perform the operations. The operation of the apparatus depicted in FIG. 1 can also be partially automated such that certain processes are under computer control and others are under operator control. Control may also be implemented over a network connection, including by a remote user over the internet.

In this embodiment, the analysis unit 210 is not integrated with the apparatus, but is rather only connected to the apparatus via piping and tubing. But in certain embodiments the analysis unit 219 could be included in the same housing as other units.

As depicted in FIG. 1, the analysis unit 210 is a laser spectrometer, specifically, a CRDS unit 210. Here, isotopic analysis data from the CRDS unit are improved by separation and purification of specific components from the gas sample before analysis is performed. By introducing only a single, relatively pure component into the CRDS unit 210, interference from other components (or impurities) is reduced or eliminated and the quality of spectroscopic data is significantly improved. Thus, rather than performing analysis on a constantly varying mixture of components, the analysis can be performed on the component of interest (e.g., methane) in relatively pure form. The analysis can also be performed in a batch or static process, rather than in continuous flow.

Furthermore, the collection of a component in a sample collector (e.g., Bag 1, Bag 2, or Bag 3) prior to distribution to analysis unit 210 allows the entire component eluting from the chromatographic column (111 or 112) to be collected. This eliminates the potential effect of isotopic fractionation that occurs as a gas component exits a chromatographic column. The collection before distribution also means that it is unnecessary to precisely synchronize the analysis unit 210 with the elution peaks coming off the separation columns 111/112.

Additionally, since the component is collected in a sample collector before distribution for analysis, it is possible to divide the collected sample into two or more portions and then perform separate analysis on the portions. The same or different analysis can be performed on the portions. Multiple analyses on a collected sample can be used for quality control purposes to help assure operators that analytic results are correct.

A CRDS unit 210 can be used, for example, to determine the isotopic ratio $^{13}C/^{12}C$ of methane ($\delta^{13}C$) in the gas sample. It is also possible to measure hydrogen isotopic ratios $^2H/^1H(\delta D)$ of methane using CRDS technology.

Second Example Embodiment

Figure 2:
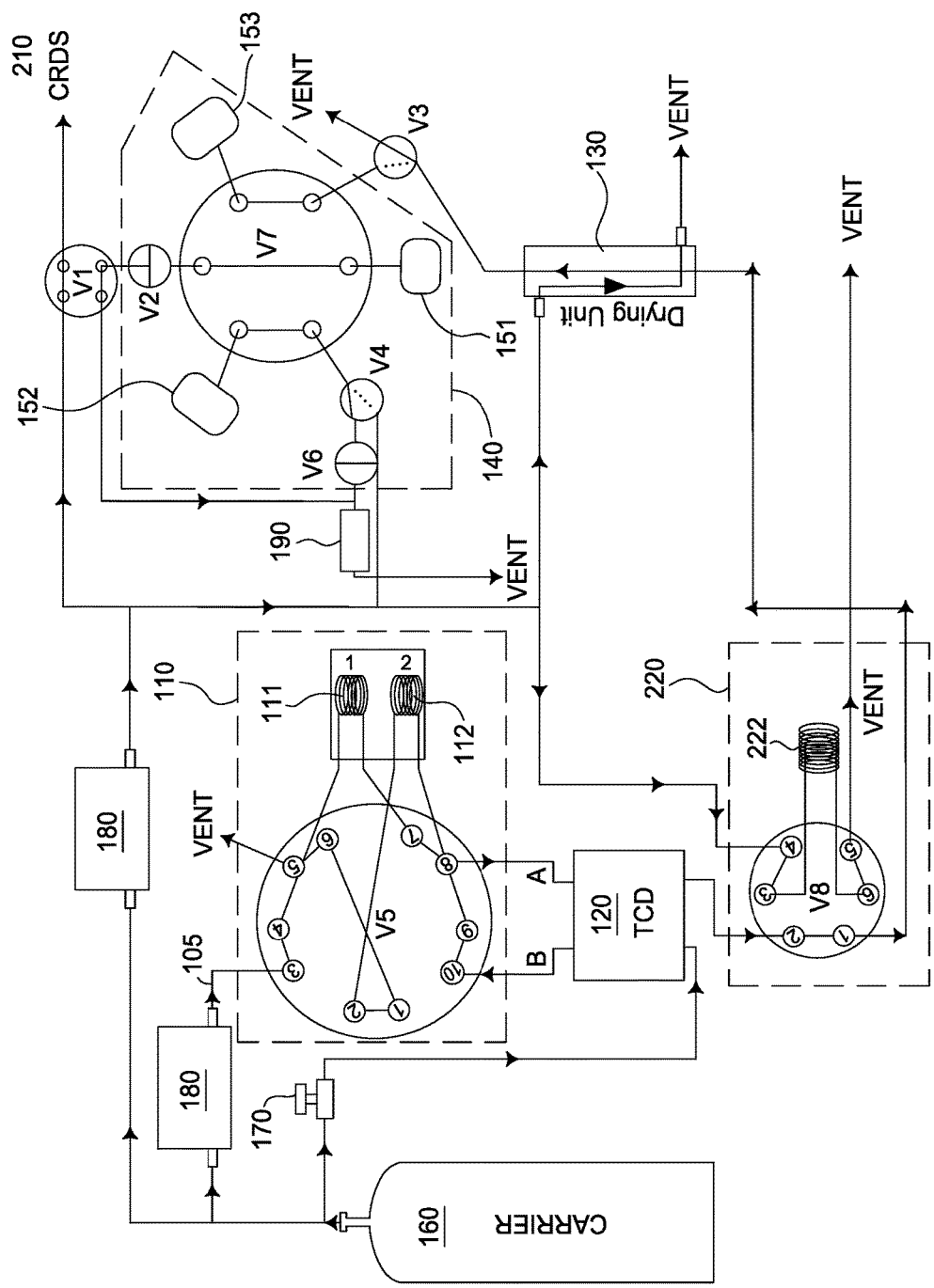
FIG. 2 is a conceptual schematic diagram depicting a second embodiment of an apparatus for preparing a gas sample for analysis.

FIG. 2 depicts, in schematic diagram, a second embodiment of an apparatus for preparing a gas sample for analysis. The second embodiment incorporates a combustion unit, but is otherwise conceptually similar to the first embodiment depicted in FIG. 1. Where description overlaps with the first embodiment, it will not be repeated.

The combustion unit 220 is configured to receive the output of the separation unit 110. Within a combustion chamber 222 of the combustion unit 220, hydrocarbons are converted in a combustion-type reaction to carbon dioxide and/or carbon monoxide. The conversion of hydrocarbons into carbon dioxide (or carbon monoxide) is necessary for some analytic methods. Specifically, in the example depicted in FIG. 2, the CRDS unit 210 used for component analysis cannot directly measure concentrations or isotopic ratios for those hydrocarbons larger than methane (e.g., ethane and propane). For example, to analyze a mudgas sample containing ethane and propane components with a CRDS system 210, it would be necessary to first convert those components to carbon dioxide prior to component collection.

The combustion unit 220 may comprise a furnace containing nickel, platinum, and cupric oxide (CuO) catalysts within in a quartz reactor as a combustion chamber 222. But preferably the combustion unit 220 may comprise lengths of platinum and copper wiring within a length of nickel tubing as the combustion chamber 222. The nickel tubing containing the platinum and copper wiring may be wrapped around a standard cartridge-type heater. When the copper wiring is heated in the presence of air (such as used as the carrier gas), the copper is converted to cupric oxide.

As depicted in FIG. 2, the combustion unit 220 may include valves (e.g., V8) and tubing which allow the combustion unit to be selectively bypassed, for example, when the component eluting from the chromatographic column 111/112 is not combustible (e.g., $CO_2$, $H_2O$, $N_2$) or if it is unnecessary to combust the component for analysis (e.g., $CH_4$). Control of the combustion unit 220 may be automated separately or integrated with other units of the apparatus.

Third Example Embodiment

Figure 3:
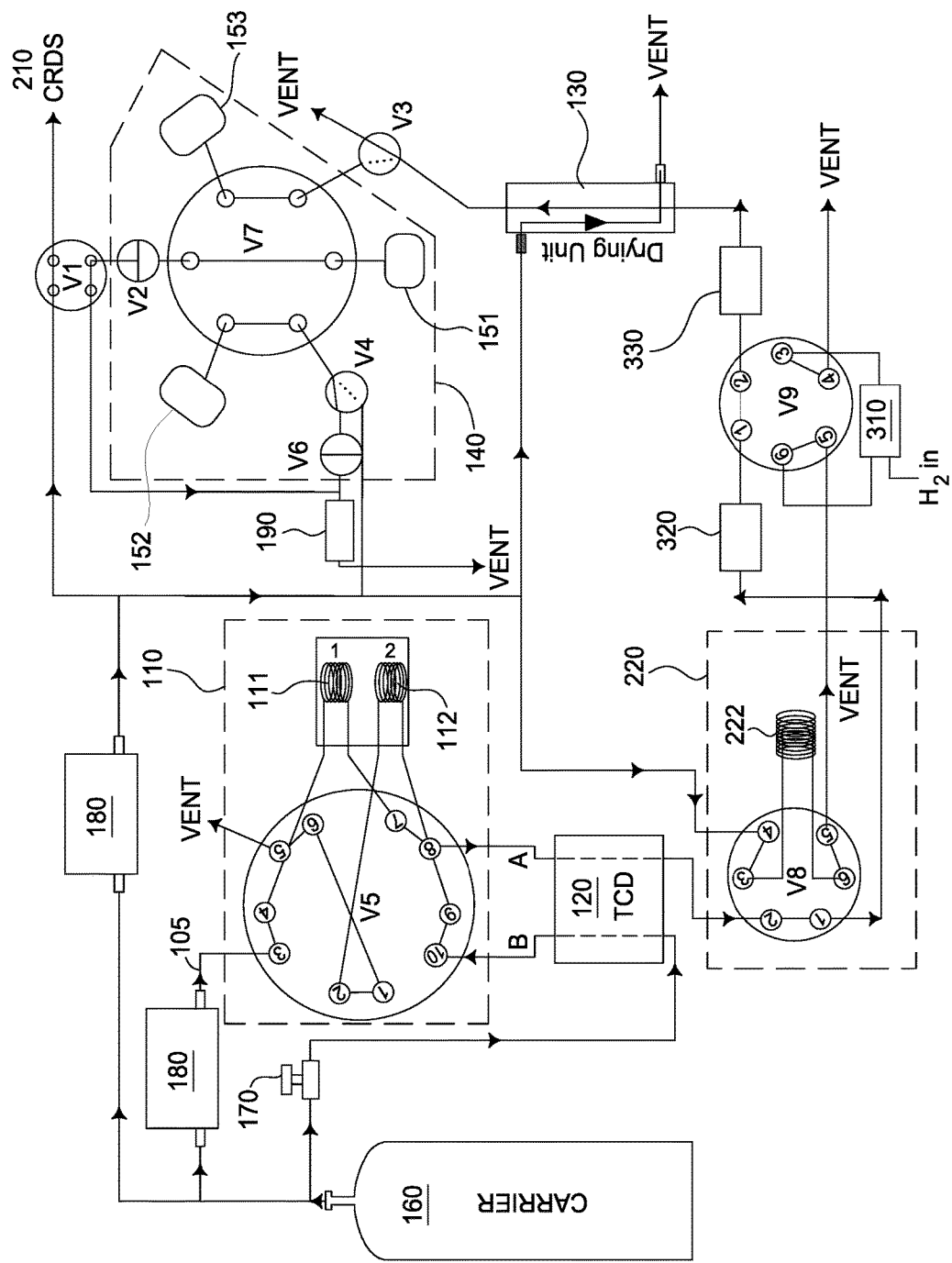
FIG. 3 is a conceptual schematic diagram depicting a third embodiment of an apparatus for preparing a gas sample for analysis.

FIG. 3 depicts, in schematic diagram, a third embodiment of an apparatus for preparing a gas sample for analysis. The third embodiment incorporates a methanizer unit 310, but is otherwise conceptually similar to the second embodiment depicted in FIG. 2. Where description overlaps with the second embodiment, it may not be repeated.

A methanizer unit 310 converts carbon dioxide or carbon monoxide into methane by a catalytic reduction reaction. In the methanizer unit 310 depicted in FIG. 3, a feed stream of hydrogen is reacted with combustion products (e.g., carbon dioxide or carbon monoxide) from combustion unit 220 over a heated nickel catalyst to generate methane. The mix of combustion products from combustion unit 220 depends on a variety of operating conditions and design choices. For example, operating the combustion unit 220 with a low oxygen mix in the combustion chamber 222 may result in carbon monoxide as a primary combustion product rather than carbon dioxide. The combustion products may also be a mixture of carbon dioxide and carbon monoxide. The methanizer unit 310 may operate with higher efficiency when the combustion product includes primarily carbon monoxide as the primary reduction reaction pathway from carbon dioxide to methane is a two step reaction having a carbon monoxide intermediary.

The combustion products quantities correspond to quantity of hydrocarbon components present in the gas sample input to the separation unit 110. By combusting hydrocarbon components to carbon dioxide (or carbon monoxide), then converting these combusted components into methane, it is possible to take advantage of the much lower detection limits of methane relative to carbon dioxide/carbon monoxide in a CRDS unit 210 (or other analysis unit 210). For example, using the methanizer unit 310 to convert $CO_2$ from the combustion of hydrocarbons such as ethane, propane, butane, pentane, or even larger molecules into methane permits isotopic analysis of those components at concentrations two orders of magnitude lower than analyzing the $CO_2$ directly in a CRDS unit. The methanizer unit 310 thus allows for analysis of low concentration components such as ethane, propane, butane, and pentane in mudgas samples, for example by converting these components to more readily analyzable methane.

In some embodiments, an oxygen removal unit 320 may be incorporated. Oxygen removal unit 320 operates to remove excess oxygen from the carrier gas before the combustion products are feed to the methanizer unit 310. When air is used as the carrier gas, oxygen removal unit 320 may be required prevent the preferential reaction of hydrogen gas fed to the methanizer unit 310 with the oxygen in the carrier gas accompanying the combusted component sample. There are a variety of techniques for removing/scrubbing excess oxygen from the carrier gas. For example, a hot copper furnace can be used to react with the oxygen in the carrier gas. Copper at elevated temperature (such as approximately 500° C. or greater) reacts quantitatively with oxygen. The copper reacted with oxygen in such a manner can be regenerated by using hydrogen gas.

Depending on the type of analysis unit 210 adopted, it may be necessary or preferable to remove hydrogen from the sample stream prior to sample collection or analysis. A hydrogen scrubber unit 330 may be incorporated in the post-methanizer flow stream, as depicted in FIG. 3, if necessary. A variety options are known to be available for hydrogen scrubber unit 330. As one example, a palladium filter can be incorporated into hydrogen scrubber unit 330.

An additional valve V9 may be incorporated to allow for methanizer unit 310 to be bypassed as desired and/or connect the output of methanizer unit 310 selectively to the drying unit 130 or a vent outlet.

Other catalysts known in the art may be substituted for the heated nickel catalyst to achieve the same or similar results, but nickel is a relatively inexpensive material that is compatible with the use of compressed air as the carrier gas in the system.

The hydrogen gas used in this example may be provided from a storage source, such a compressed gas cylinder or tank, or may be generated as required by electrolysis of water or other means known in the art, such as steam reforming of hydrocarbons. On-site production of hydrogen gas may have benefits since shipment of compressed hydrogen to remote drill sites may be difficult.

Fourth Example Embodiment

FIG. 4 depicts, in schematic diagram, a fourth embodiment of an apparatus for preparing a gas sample for analysis. The fourth embodiment is conceptually similar to the first embodiment depicted in FIG. 1. Where description overlaps with the first embodiment, it may not be repeated.

The fourth embodiment includes a sampling system 400 configured for periodic or occasional sampling of a continuous gas stream (e.g., mudgas) supplied via needle valve 410. Samples are withdrawn from the continuously flowing gas stream and supplied as desired to the separation unit 110. The configuration of the fourth embodiment is particularly suitable for placement of the apparatus at the drill site where a continuous stream of mudgas is available Here, the gas sampling system includes switching valves through which a continuous stream of gas can flow. In an initial state, the gas stream flows into the system, passes through a sample loop 440 (depicted as a thick line in sampling system 400) to vent or another sampler system (e.g., an autosampler). When a sample from the gas stream is desired, the valve(s) V10 and/or V11 switch and the gas sample presently in the sample loop 440 is supplied to the separation unit 110. The sample loop 440 (i.e., the loop through which gas was flowing through in the initial state) is, in the next state, connected to a gas chromatographic column 111/112 in the separation unit 110 and the carrier gas input flow. The sample loop 440 can be sized to supply a desired volume of gas to the separation unit 110.

This fourth embodiment also includes an optional reference standard gas supply 450, which allows periodic or occasional calibration of the analysis unit 210 and overall system checks. The standard gas supply 450 contains known concentrations of analytes, so measurement results from the attached or integrated analysis unit 210 can be checked against known values. The gas sample injection system 440 receives the standard gas and by operation of the valve(s) (e.g., needle valve 420, valve V10, and valve V11) can flow the standard gas through a sample loop 440 to thereby supply the standard gas sample to the separation unit 110.

The fourth embodiment may also be combined and utilized with the second and third embodiments. That is the sampling system 400 of the fourth embodiment can be incorporated in an apparatus with a combustion unit 220 and/or a methanizer 310.

Fifth Example Embodiment

In a fifth embodiment of an apparatus for preparing a gas sample for analysis is configured to use molecular sieves as a sample collector (or sample collectors), rather than gas bags. That is, for example, in FIG. 1 sample collectors 151, 152, 153 may comprise molecular sieve components. The molecular sieves are used to collect combustion products for isotopic analysis. Molecular sieves are typically used in certain elemental analyzers, but are not used in natural gas analysis or otherwise coupled with a GC separation system, as depicted here. When molecular sieves are used it is possible to collect water generated by the combustion of a component sample. Between collections molecular sieves can be heated to drive off previously collected water or other components. In this fifth embodiment, the analysis unit 210 may comprise two or more CRDS units, one of which may be dedicated to the analysis of collected water from combustion of the component sample.

The molecular sieve sample collectors of the fifth embodiment could also be used in the first, third, and fourth embodiments, or combinations thereof. Using molecular sieves as sample collectors has at least two advantages. One being that the amount of required dilution by the carrier gas will generally be lower, which would allow lower concentrations of hydrocarbons to be analyzed, particularly if the products from combustion were first converted to $CH_4$ in a methanizer. Another being it would allow analysis of the hydrogen isotope compositions of hydrocarbon gas samples by allowing the collection of water resulting from the combustion of the hydrocarbon sample.

Other Embodiments

In general, any of the described embodiments may be combined with other embodiments without departing from the scope of this disclosure.

The apparatus for preparing a gas sample for analysis can be integrated with an analysis unit 210, such as a laser spectrometer. The laser spectrometer may be, for example, a CRDS system. The sample preparation apparatus may be included in or on the same housing, box, chassis as the analysis unit 210 to form a unitized apparatus. It is also possible that only portions of the sample preparation apparatus are incorporated with the analysis unit 210. For example, only the sample collection unit 140 may be integrated with the analysis unit and other portions of the sample preparation apparatus may remain a discrete unit or units.

When the analysis unit 210 is, for example, a CRDS unit 210, it is possible to operate the analysis unit 210 in a static mode rather than continuously flowing gas through the unit. That is, a small volume of component sample gas may be introduced into the CRDS unit 210 from the sample collector unit 140 and this small volume can then be analyzed discretely. This allows greater control over the operating pressure and temperature, which generally leads to better precision in isotopic ratio or other data.

Additionally, static operation generally requires less total component sample volume, which may be advantageous from the standpoint of, for example, throughput and/or equipment sizing. Also, as mentioned previously, if only a portion of the collected component sample is consumed by each analysis procedure, it is possible to perform multiple analyses on each collected component sample. Multiple analyses can be used to further increase confidence in analytic data from the gas sample. The multiple analysis procedures may be performed serially in the same analysis unit 210 or in parallel in different analysis units 210. The different analysis units 210 can all use the same technology (e.g., all CRDS units) or can use different technologies.

In operation of an analysis unit 210, such as a CRDS unit 210, in static mode, a measurement chamber may first be evacuated and flushed with a purge gas (e.g., the carrier gas), the sample component gas is then streamed to the measurement chamber until a desired operating pressure is achieved.

Once the desired operating pressure is achieved, the measurement chamber can be closed by, for example, closing valves at the inlet and outlet of the chamber. The sample in the measurement chamber can then be analyzed immediately thereafter, or potentially after some period of time to allow the gas sample and chamber to equilibrate. Operation in static mode eliminates errors caused by pressure variances and possibly changing concentrations of the analyte in the chamber due to sample flow variances or the like.

The inclusion of a thermal conductivity detector (e.g., TCD 120) in the sample preparation apparatus allows for the quick determination of whether the methane concentration in a sample exceeds the linear detection range of the analysis unit 220. The TCD 120 can be used to estimate concentration of sample components based on detected eluted component peak heights. If the methane concentration exceeds the maximum allowable concentration, the methane concentration can be diluted by flowing additional carrier gas into the sample collector. The dilution processes can be automated and implemented in control software. If other sample components exceed a range acceptable to the analysis unit 210, these other components can likewise be diluted in a manner similar to methane.

Disclosed methods of operation of a sample preparation apparatus and a gas sample analyzer may be implemented, fully or partially, as computer software programs stored in non-transitory, computer-readable media. Where computer control is possible, such control may be made via a network (including the Internet).

While the foregoing is directed to example embodiments of the present disclosure, other and additional embodiments may be devised without departing from the basic scope thereof, and the scope thereof is determined by the claims that follow.

The invention claimed is:

1. A method of preparing a sample for analysis, comprising:
    separating a gas sample into at least one component sample in a separation unit;
    detecting an output of the at least one component sample from the separation unit;
    combusting a hydrocarbon in the at least one component sample in a combustion unit to generate a combustion product;
    collecting the combustion product in a sample collector; and
    supplying the collected combustion product to an analysis unit.

2. The method of claim 1,
    wherein the combustion product is at least one of carbon dioxide and carbon monoxide.

3. The method of claim 1, wherein the combustion unit comprises a gas combustion chamber.

4. The method of claim 3, wherein the gas combustion chamber includes copper wire and platinum wire within a tubing comprising nickel.

5. The method of claim 1, wherein the analysis unit is a cavity ring down spectrometer.

6. The method of claim 5, wherein the cavity ring down spectrometer is operated in a static mode.

7. The method of claim 1, further comprising:
    analyzing the combustion product in the analysis unit to determine an isotopic ratio of the at least one component sample.

8. The method of claim 7, wherein the isotopic ratio is a carbon isotopic ratio.

9. The method of claim 1, wherein a thermal conductivity detector is used for detecting the output of the at least one component sample from the separation unit.

10. The method of claim 1, further comprising:
supplying the gas sample to the separation unit from a continuous gas flow.

11. The method of claim 10, wherein the continuous gas flow is a mudgas stream from a wellbore.

12. The method of claim 1, wherein the separation unit is a chromatographic column.

13. The method of claim 1, further comprising:
removing water from the at least one component sample.

14. The method of claim 1, further comprising:
supplying air as a carrier gas to the separation unit and the sample collector.

15. A method of analyzing mudgas components, comprising:
supplying a mudgas sample to a gas chromatograph to separate the mudgas sample into different components on the basis of component elution times;
detecting an output of at least one component of the mudgas sample from the gas chromatograph using a thermal conductivity detector;
supplying the at least one component to a combustion chamber and combusting a hydrocarbon in the at least one component to form a combusted component sample including at least one of carbon dioxide and carbon monoxide;
collecting the combusted component sample in a sample collection unit; and
supplying the combusted component sample from the sample collection unit to an analysis unit.

16. The method of claim 15, further comprising:
converting carbon dioxide or carbon monoxide in the combusted component sample to methane before supplying the combusted component sample to the analysis unit.

17. The method of claim 15, further comprising:
determining a carbon isotopic ratio in the mudgas sample based on an analysis of the combusted component sample in the analysis unit.

* * * * *